(12) United States Patent
Mooney et al.

(10) Patent No.: US 8,911,388 B2
(45) Date of Patent: Dec. 16, 2014

(54) METHOD AND DEVICE FOR SPINAL TRACTION ALIGNMENT

(71) Applicants: Joseph P Mooney, Pikeville, NC (US); William C Reavis, North Myrtle Beach, SC (US); Amanda Mooney, Pikeville, NC (US)

(72) Inventors: Joseph P Mooney, Pikeville, NC (US); William C Reavis, North Myrtle Beach, SC (US); Amanda Mooney, Pikeville, NC (US)

(73) Assignee: Bobby B. Reavis, Goldsboro, NC (US)

( * ) Notice: Subject to any disclaimer, the term of this patent is extended or adjusted under 35 U.S.C. 154(b) by 122 days.

(21) Appl. No.: 13/625,907

(22) Filed: Sep. 25, 2012

(65) Prior Publication Data

US 2014/0088480 A1    Mar. 27, 2014

(51) Int. Cl.
*A61F 5/00* (2006.01)
*A61F 5/37* (2006.01)

(52) U.S. Cl.
USPC ............................. 602/32; 128/870

(58) Field of Classification Search
CPC .................................................. A61H 1/0218
USPC ........ 128/845, 846, 870, 871, 133; 602/32, 1; 600/15; 601/316; D24/200; 5/630, 731, 5/652
See application file for complete search history.

(56) References Cited

U.S. PATENT DOCUMENTS

| | | | | |
|---|---|---|---|---|
| 726,054 A | * | 4/1903 | Hartford | 606/240 |
| 726,055 A | * | 4/1903 | Hartford | 606/240 |
| 1,572,794 A | * | 2/1926 | Hamilton | 606/240 |
| 1,833,426 A | * | 11/1931 | Knudson | 606/240 |
| 4,230,099 A | * | 10/1980 | Richardson | 606/240 |
| 5,007,414 A | * | 4/1991 | Sexton | 602/19 |
| D321,402 S | * | 11/1991 | Hoshino | D24/188 |
| 5,925,003 A | * | 7/1999 | Vincent et al. | 601/134 |
| 6,036,719 A | * | 3/2000 | Meilus | 606/204 |
| 8,434,492 B2 | | 5/2013 | Jones | |
| 8,496,007 B2 | * | 7/2013 | Rambo et al. | 128/845 |
| 8,696,607 B2 | * | 4/2014 | McDonnell et al. | 601/134 |
| 2010/0236560 A1 | | 9/2010 | Rambo et al. | |

FOREIGN PATENT DOCUMENTS

| | | |
|---|---|---|
| EP | 2158893 A1 | 3/2010 |
| JP | 2002253702 A | 9/2002 |
| SU | 415010 A1 | 6/1974 |

OTHER PUBLICATIONS

US Therapy, Inc., The Benefits of Using the Spine-Worx Alignment System, http://www.spineworx.com/404565.html.
PCT/US2013/061610 Search Report and Written Opinion; Mar. 13, 2014.

* cited by examiner

*Primary Examiner* — Patricia Bianco
*Assistant Examiner* — Tarla Patel
(74) *Attorney, Agent, or Firm* — James G. Passe; Passe Intellectual Property, LLC

(57) ABSTRACT

The present invention relates to a device for providing passive traction involving a pair of rails with 8 degrees of freedom and matching the user's spinal curve for providing relaxation and other medical treatment to a user.

5 Claims, 3 Drawing Sheets

METHOD AND DEVICE FOR SPINAL TRACTION ALIGNMENT

COPYRIGHT NOTICE

A portion of the disclosure of this patent contains material that is subject to copyright protection. The copyright owner has no objection to the reproduction by anyone of the patent document or the patent disclosure as it appears in the Patent and Trademark Office patent files or records, but otherwise reserves all copyright rights whatsoever.

BACKGROUND OF THE INVENTION

1. Field of the Invention

The present invention relates to a device for providing passive traction to the spinal column. In particular, the present invention relates to a device for providing passive traction to the spinal column and can self adjust to movements of users of the device.

2. Description of Related Art

The use of passive traction to provide relief and prevention of back trouble arising from muscle and spinal tensions has long been known. Relief of such tensions and strain has known use in preventing injury, relieving tension, and preventing a wide array of disease and medically difficult conditions.

A wide variety of treatments and devices have been used to relieve such tensions and one of the primary functions of a chiropractor is to relieve such tension. Passive devices for such treatment which avoid a chiropractor usually rely on the weight of the user and the force of gravity to achieve the traction of the musculature surrounding the spinal column.

One approach to passive spinal column traction is depicted in US patent publication US 2010/0236560 wherein a convex asymmetrical longitudinal curve, a central longitudinal groove, and mirrored perpendicular and latitudinal symmetrically-matched convex curves (rails) extending from the central groove to the sides and optimally surfaced with a soft sense foam which uses gravitational force on the body of a user to provide traction. While traction is provided, the user must lie perfectly still or the traction provided becomes uneven or non-existent during the process of using the device.

BRIEF SUMMARY OF THE INVENTION

The present invention relates to the surprising discovery that if the parallel rails of a spinal gravity traction device are allowed to move with eight degrees of freedom relative to one another as a person lying on the device shifts their weight on it, that the device can provide even traction pressure and relief.

Accordingly, in one embodiment the present invention comprises an adjustable passive gravity spinal traction device for a human to lie upon comprising:
   a) a first rail having the length and curve of an anatomically correct human spine mounted on a base;
   b) a second rail having the length and curve of an anatomically correct human spine mounted on a base; and
   c) a connector for connecting the first and second rail together such that they can move in an adjustment of eight degrees of freedom relative to one another as the human lies on the first and second rail in a manner such that the human remains in contact with the first and second rails as the human shifts their weight.

In another embodiment there is a method of using a two rail adjustable passive gravity spinal traction device with a human comprising:
   a) positioning the adjustable passive gravity spinal traction device on a surface; and
   b) positioning the human on the adjustable passive gravity spinal traction device such that muscles on the left side of a spinal column of the human are supported on a first rail and muscles on the right side of the spinal column of the human are supported on a second rail such that portions of the spinal column of the human are disposed unsupported in a trough between the first rail and the second rail.

DETAILED DESCRIPTION OF THE INVENTION

Figure 1:
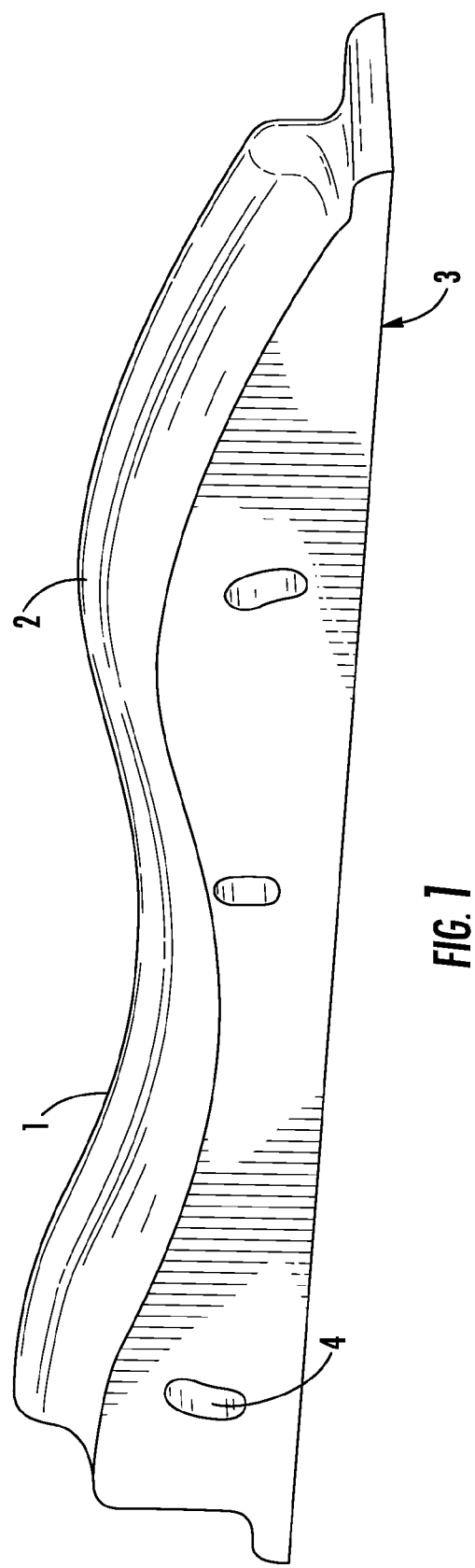
FIG. 1 is a perspective view of a first rail.

While this invention is susceptible to embodiment in many different forms, there is shown in the drawings and will herein be described in detail specific embodiments, with the understanding that the present disclosure of such embodiments is to be considered as an example of the principles and not intended to limit the invention to the specific embodiments shown and described. In the description below, like reference numerals are used to describe the same, similar or corresponding parts in the several views of the drawings. This detailed description defines the meaning of the terms used herein and specifically describes embodiments in order for those skilled in the art to practice the invention.

DEFINITIONS

The terms "about" and "essentially" mean ±10 percent.

The terms "a" or "an", as used herein, are defined as one or as more than one. The term "plurality", as used herein, is defined as two or as more than two. The term "another", as used herein, is defined as at least a second or more. The terms "including" and/or "having", as used herein, are defined as comprising (i.e., open language). The term "coupled", as used herein, is defined as connected, although not necessarily directly, and not necessarily mechanically.

The term "comprising" is not intended to limit inventions to only claiming the present invention with such comprising language. Any invention using the term comprising could be separated into one or more claims using "consisting" or "consisting of" claim language and is so intended.

Reference throughout this document to "one embodiment", "certain embodiments", and "an embodiment" or similar terms means that a particular feature, structure, or characteristic described in connection with the embodiment is included in at least one embodiment of the present invention. Thus, the appearances of such phrases or in various places throughout this specification are not necessarily all referring to the same embodiment. Furthermore, the particular features, structures, or characteristics may be combined in any suitable manner in one or more embodiments without limitation.

The term "or" as used herein is to be interpreted as an inclusive or meaning any one or any combination. Therefore, "A, B or C" means any of the following: "A; B; C; A and B; A and C; B and C; A, B and C". An exception to this definition will occur only when a combination of elements, functions, steps or acts are in some way inherently mutually exclusive.

The drawings featured in the figures are for the purpose of illustrating certain convenient embodiments of the present invention, and are not to be considered as limitation thereto. Term "means" preceding a present participle of an operation indicates a desired function for which there is one or more embodiments, i.e., one or more methods, devices, or apparatuses for achieving the desired function and that one skilled in the art could select from these or their equivalent in view of the disclosure herein and use of the term "means" is not intended to be limiting.

As used herein an "adjustable passive gravity spinal traction device" refers to a dual rail traction device for supporting the spinal column and providing traction of the surrounding musculature. It is designed for a person (human) to lie upon wherein the weight of the user and the force of gravity produce the traction. The rails are designed in the natural curve of the spinal column such that when the user lies upon the traction device one rail is positioned on either side of the spinal column and the curves of the rails match the curves of the spine. The length will obviously be variable based on the individual user using the device (e.g. height and weight) but a single size could be used for as much as 30% differences in alignment. Those skilled in the art of making such traction devices would be aware of the types of materials the device can be constructed of, for example, plastics such as polyethylene (e.g. a self skinning poly urethane), wood, recycled material, metals, or the like can all be utilized in the construction of the traction device. The device can be solid or hollow and in some instances can be made of mixed (i.e. more than one different) material. They may be shaped by any convenient means such as molding, carving, gluing, or the like. While the device in one embodiment would be approximately 18 to 31 inches in length, the length will be essentially matched to the user.

As used herein the rails "moving in an adjustment of eight degrees of freedom" refers to the present invention wherein the rails are connected to one another as the user lies upon the device but the rails can, in limited fashion, move relative to one another in the eight degrees of freedom although limited to a few centimeters to a few inches in movement. By "connected" is meant that the two rails cannot move farther apart than a certain distance dictated by the degrees of movement allowed by the device. In one embodiment, the rails are mounted on their base and allowed to move relative to one another by movement on the base. The base mounting allows them to be connected indirectly rather than directly to each other.

As used herein a "human" refers to a human user utilizing the device. A user will, therefore, be a synonym for a human as used herein.

As used herein a "rail" refers to a long independent rail, each rail having a convex top surface, an asymmetrical longitudinal curve, and one half of a central longitudinal groove (this can clearly be seen in each of the figures provided herein of the general curves of the human spinal column). When the two rails are connected by whatever means, they form a central hollow space allowing a space for the user's vertebrae to be at least partially or completely suspended in between the rails to provide traction. By necessity, the rails will always be of a denser material than a cover, if a cover is utilized.

As used herein a "base" refers to whatever shape device or the like the rails are mounted on in order to be able to place them on a surface for use. In many cases, there is a flat base which allows the device to be placed on a table or other flat surface (horizontal or inclined as desired) to provide appropriate place. The device could be placed or attached to other devices to provide traction during use of whatever the device is mounted on. Examples of where the device could be mounted on include the back rest of an exercise machine, a vehicle seat, a bed, back pack frame, a gravity inversion table, a recliner style chair, or the like.

As used herein a "connector" refers to a means for keeping the two rails limited in their position relative to one another. Mounting on bases that are fixed relative to one another is one method, however, directly connecting by using a slot and pin design (as shown in the figures) with adjustable tensioning fasteners such as adjustable mating screws allows for an adjustment or limitation of how much force is necessary to achieve eight-way adjustment. In one embodiment of slot and pins, there are three pins, the center pin acting as an axis in a fixed position along with the other two pins on one rail which allows for eight-way movement. Associated slots on the other rail allow movement in the eight-way but in a limited fashion as desired. The eight-way movement is just enough to accommodate the movement of a user on the device during use of the device. Fastener pins or mating screws can be utilized to hold the rails together in an embodiment and can be adjusted in tightness to accommodate the level of friction between the two rails.

Normally a user lying on the device as they shift their weight will cause the rails to move relative to one another but by adjusting the tension, one can compensate for different weight users and other conditions as desired. This way the rails will track the user and will remain in contact with the back as compared to a fixed rail system.

As used herein a "contoured foam body" refers to the device being encased in a contoured foam body. The foam body should be of even thickness and smooth on the rails themselves to accommodate the user and not create pockets of varying pressure due to thickness differences. However, varying thicknesses at various positions could be utilized. This foam could be open cell type foam, foam rubber, or the like but any soft foam or foam like material could be utilized including organic materials such as cotton, hemp, and the like. The foam encasement is manufactured and assembled by those means known in the art for these types of foam encasements. In one embodiment, the contours of the foam encasement allow for a concave section at the user's head to level the head allowing the cervical portion of the rails to be in contact with the neck and or a raised lateral convex shape to support the neck as required by the user to allow for the self alignment of the spinal column.

Other additional devices can be included with the traction device including a heating device, a cooling device, magnets (especially therapeutically positioned), and a vibration device. Others include cold light lasers which stimulate circulation such as those made by anodyne. The use of these additional elements is within the skill in the art in view of this disclosure.

In order to use the adjustable passive gravity spinal traction device of the present invention the user lies on the device such that positioning the human on the adjustable passive gravity spinal traction device such that muscles on the left side of a spinal column of the human are supported on a first rail and muscles on the right side of the spinal column of the human are supported on a second rail such that portions of the spinal column of the human are disposed unsupported in a trough between the first rail and the second rail.

Now referring to the drawings. FIG. 1 is a perspective view of a first rail. First rail 1 consists or anatomical spinal column rail 2, base 3, and connector slots 4 for a pin and slot attachment and eight-way movement. This particular base 3 is designed for a flat surface but other bases could be anticipated as discussed above.

Figure 2:
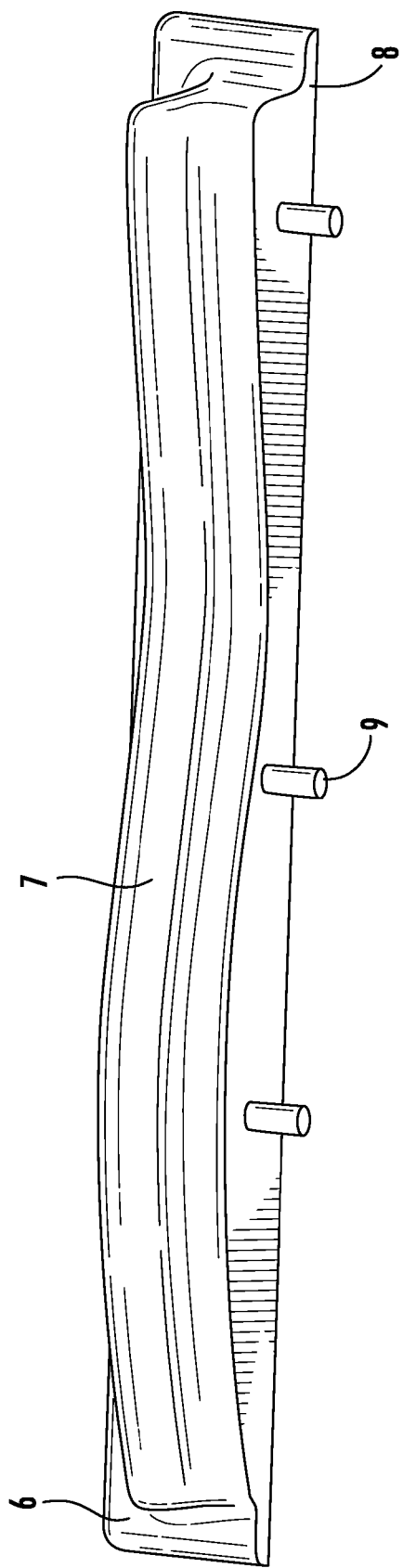
FIG. 2 is a perspective view of a second rail.

FIG. 2 is a perspective view of a second rail 6 which has a second anatomical spinal column rail 7. The second rail 6 has a base 8 and the second rail 6 has pins 9 for mating with the slots 4 of rail 2 and connecting the two rails together.

Figure 3:
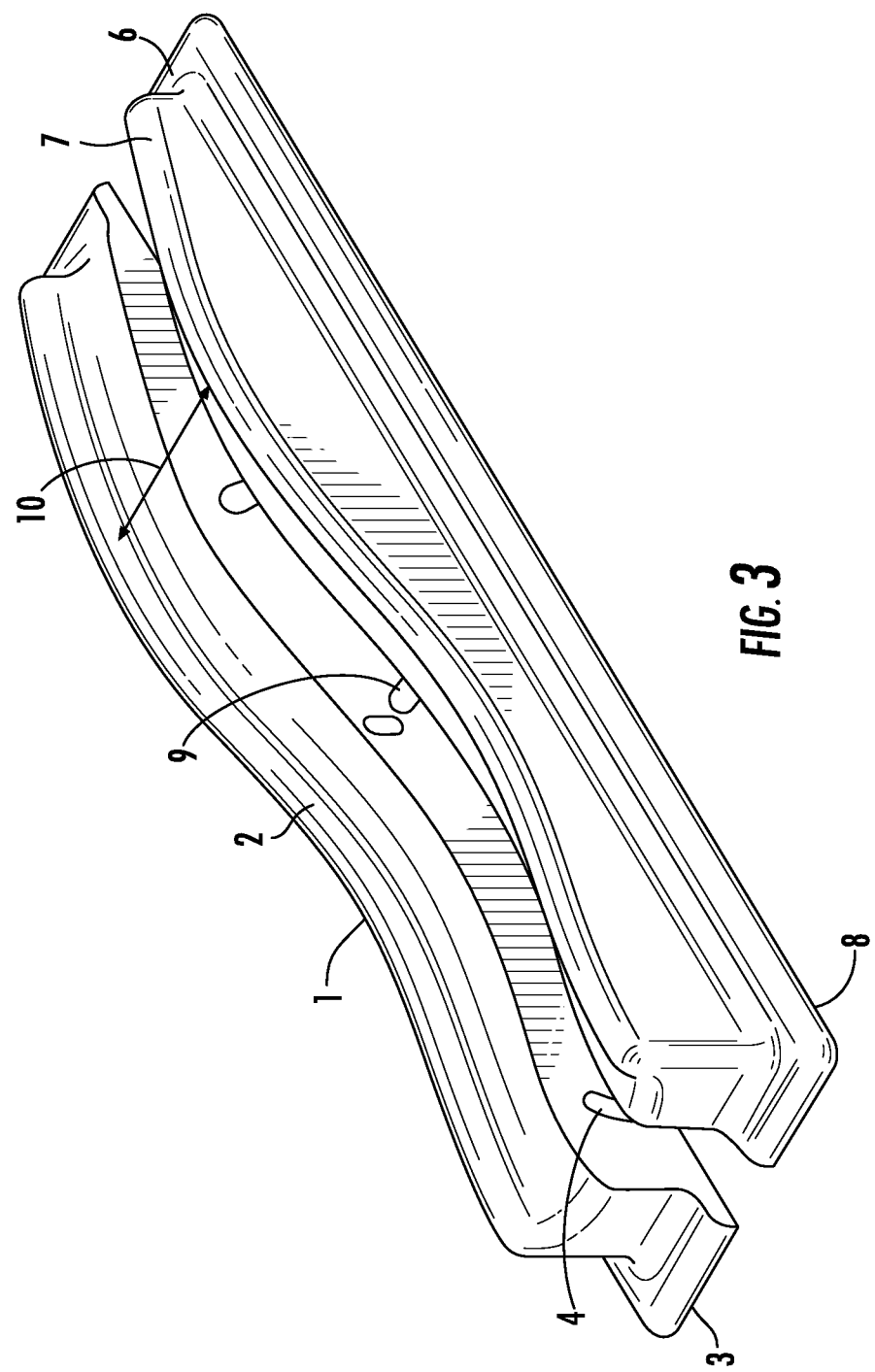
FIG. 3 is an exploded view of the adjustable passive gravity spinal traction device of the invention.

FIG. 3 is an exploded view of the adjustable passive gravity spinal traction device of the invention. The two rails come together matching the rods 9 and slots 4 to make a single device. The two rails form a concave depression 10 which allows the user's spinal column to hang down and the user to receive traction during use.

Those skilled in the art to which the present invention pertains may make modifications resulting in other embodiments employing principles of the present invention without departing from its spirit or characteristics, particularly upon considering the foregoing teachings. Accordingly, the described embodiments are to be considered in all respects only as illustrative, and not restrictive, and the scope of the present invention is, therefore, indicated by the appended claims rather than by the foregoing description or drawings. Consequently, while the present invention has been described with reference to particular embodiments, modifications of structure, sequence, materials and the like apparent to those skilled in the art still fall within the scope of the invention as claimed by the applicant.

What is claimed is:

1. An adjustable passive gravity spinal traction device for a human to lie upon comprising:
   a) a first rail having the length and curve of an anatomically correct human spine mounted on a base;
   b) a second rail having the length and curve of an anatomically correct human spine mounted on a base;
   c) wherein the rails are free to move relative to one another in eight degrees of freedom, and
   d) a connector between the two rails for limiting the relative movement to of the rails just enough to accommodate the movement of the human using the device.

2. The adjustable passive gravity spinal traction device according to claim 1 wherein the device is encased in a contoured foam body.

3. The adjustable passive gravity spinal traction device according to claim 1 wherein the connector comprises a slot and pin design.

4. The adjustable passive gravity spinal traction device according to claim 3 wherein the slot and pin design comprises adjustable tensioning fasteners.

5. A method of using a two rail adjustable passive gravity spinal traction device with a human comprising:
   a) positioning the adjustable passive gravity spinal traction device on a surface; and
   b) positioning the human on the adjustable passive gravity spinal traction device such that muscles on the left side of a spinal column of the human are supported on a first rail and muscles on the right side of the spinal column of the human are supported on a second rail such that portions of the spinal column of the human are disposed unsupported in a trough between the first rail and the second rail.

* * * * *